United States Patent [19]

Fey

[11] Patent Number: 4,832,994

[45] Date of Patent: May 23, 1989

[54] ANTI-SMOKING ORAL COMPOSITION

[76] Inventor: Michael S. Fey, 96 Sylvan Dr., Morris Plains, N.J. 07950

[21] Appl. No.: 92,045

[22] Filed: Sep. 2, 1987

[51] Int. Cl.⁴ .......................... A61K 9/68; A23G 3/30
[52] U.S. Cl. .......................................... 428/48; 426/3; 426/5; 424/439; 424/440; 424/464; 424/468; 424/469; 424/484; 424/485; 514/813; 514/948; 514/959; 514/964; 514/965; 514/974
[58] Field of Search ................. 426/3, 5; 424/48, 439, 424/440, 464, 468, 469, 484, 485; 514/813, 948, 959, 964, 965, 974

[56] References Cited

U.S. PATENT DOCUMENTS

| | | | |
|---|---|---|---|
| 3,075,884 | 1/1963 | Bilotti | 424/48 |
| 3,876,804 | 4/1975 | Woodcraft | 426/3 |
| 4,276,890 | 7/1981 | Fichera | 424/48 |
| 4,311,691 | 1/1982 | Fichera | 424/48 |

Primary Examiner—Ellis P. Robinson
Assistant Examiner—P. J. Ryan
Attorney, Agent, or Firm—Ronald G. Goebel; Bruce M. Collins

[57] ABSTRACT

Anti-smoking oral preparations are provided containing a silver compound as the anti-smoking agent and a sweetener in which the silver compound is present in amounts of from 0.1 mg. to 2.5 mg. and the ratio of sweetness intensity based on sucrose to silver compound content is from 100:1 to 2500:1.

6 Claims, No Drawings

ANTI-SMOKING ORAL COMPOSITION

BACKGROUND OF THE INVENTION

This invention is concerned with anti-smoking oral preparations containing silver compounds.

In recent times many studies conducted on the effects of smoking on human health have demonstrated that smoking is a health-threatening and life-threatening habit. Studies have also indicated that cessation of smoking can significantly ameliorate, if not eliminate, the adverse effects of tobacco smoking. The public awareness of the hazards of smoking and the benefits of quitting have spawned products and methods to aid the smoker in breaking the habit.

Silver salts have been used as anti-smoking agents because of their unpleasant taste which becomes accentuated when in contact with tobacco smoke. However, they cause an unpleasant taste in the mouth even in the absence of tobacco smoke and spoil the flavor of food and drink. They are also absorbed by the body and on prolonged use cause a permanent condition of the skin known as argyria which is a greyish or even black pigmentation of the skin.

In an effort to promote the anti-smoking characteristics of silver salts the art has employed methods to attenuate their toxic side effects.

For example, in U.S. Pat. No. 3,876,804 to D. Woodcraft an anti-smoking chewing gum is described containing a silver compound in which the silver is bound in complex form or a silver compound and a compound which in its dissolved state forms ions with silver to form silver complex ions. Such gum, in its preferred form, comprises silver acetate, a complexing agent such as ammonium chloride and a salivary promoter such as a co-carboxylase. Purportedly the gums overcome the disadvantages of silver salts by (a) masking the unpleasant taste of silver ions by complexing while still providing an unpleasant taste during smoking; and (b) effecting slow release of the active ingredient so that the user is not subjected to sudden high concentrations of silver salts which would occur on using a tablet, for example.

Commercial anti-smoking oral preparations as used today such as chewing gums and lozenges employ about 6 mg. of silver salt or compound and that level of silver has been deemed the quantity which will effectively raise the unpleasant bitter taste during smoking in the user while at the same time not be of such a magnitude to render the preparation toxic. An advisory review panel of the Food and Drug Administration (FDA) has even recommended a proposed dose of up to 6 mg. of silver acetate in a chewing gum every four hours but not more than 6 such doses in a 24 hour period. The gum was not to be used for more than 3 weeks.

It has now been found, according to the present invention, that it is not necessary to obtain an effective bitter taste response as a smoking deterrent using a silver compound such as silver acetate in amounts of 6 mg. or more and that complexing of such silver compounds using ammonium salts or amines is also unnecessary for taste masking or the reduction of toxicity. According to the present invention, an effective smoking deterrent response is accomplished by delivering to the mouth a small, but uniform concentration of silver ions at or within 1 to 2 hours of smoking. By employing a sweetener rather than a complexing agent in an anti-smoking oral composition the bitter taste of silver ions is substantially eliminated and the effective silver concentration necessary to provide smoking deterrence can be reduced dramatically thus reducing cost as well as the danger of toxic side effects.

SUMMARY OF THE INVENTION

The invention provides anti-smoking oral preparations such as lozenges, chewing gums, mouth rinses, breath sprays and toothpastes containing a silver compound and a sweetener wherein the silver compound is present at low levels and the sweetener to silver compound ratios are high so that the harsh taste of the silver compound is effectively masked while at the same time is in sufficient concentration to deter smoking. In a lozenge particularly, there is a slow uniform release of silver compound into the mouth gradually building up silver ion concentration rendering more efficient the role of silver as an anti-smoking agent. The low levels of silver compound also reduce the cost of the preparation and avoids toxic side effects.

DETAILED DESCRIPTION OF THE PREFERRED EMBODIMENTS

Briefly, the invention provides an effective anti-smoking oral preparation such as a lozenge, chewing gum, mouthwash, toothpaste, breath spray, or the like containing a silver compound and a sweetener which preparation contains a low concentration of silver compound and a high concentration of sweetener such as sucrose. The oral preparations according to the invention provide a uniform concentration of silver ions in the mouth whose smoking deterrency lasts up to 3 hours depending on an individual's sensitivity to the silver/smoke bitter taste. Rather than complexing silver ions with an ammonium compound or an amine to attenuate the silver ion dosage, improve taste and reduce silver absorption in the body, an acceptable and effective taste can be developed which produces a deterrent taste response to smoking based on the ratio of sweetness intensity relative to sucrose to silver compound content. Sucrose is used as a standard in the candy and confections art by which other sweeteners are rated for sweetness. For example, using 1.0 as a sweetness rating for sucrose, sweeteners such as maltose and sorbitol have a sweetness of 0.5 relative to sucrose which means that twice as much maltose or sorbitol is needed than sucrose to achieve the same sweetness intensity. Artificial sweeteners such as 6-chlorosaccharin has a sweetness rating of 200 relative to sucrose which means that only 0.005 as much 6-chlorosaccharin than sucross is needed to achieve the same sweetness intensity. Regular corn syrup for example, provides about the same sweetness as sucrose. "Sweetness intensity" as used herein means the weight of a sweetener which is equivalent to sucrose in sweetness. It has been found that the sweetness intensity/silver compound ratio should be from about 100:1 and 2500:1 and preferably between about 500:1 and 1000:1 wherein the amount of silver in the preparation is from 0.1 mg. to 2.5 mg. and preferably from 0.5 mg. to 2 mg.

The oral preparation of the invention can take the form of a lozenge, tablet, chewing gum, mouthrinse, breath spray, toothpaste or other composition. It has been found that a lozenge is most preferable because it will uniformly bathe the mouth with silver ions at low concentrations, gradually building a level of silver ions with time until the lozenge is either expelled upon smoking or dissolved completely. In either case the smoking deterrent response should last from between 1 and 3 hours.

The silver compounds useful in this invention are those capable of delivering silver ions in the oral cavity such as silver acetate and silver lactate. Silver acetate is preferred due to its water-solubility, availability and acceptability as an anti-smoking agent.

The sweeteners of the invention include mono, di and polysaccharides such as sucrose, glucose, fructose, galactose, maltose, mannose and isomaltose; polyhydric alcohols such as xylitol, sorbitol, mannitol, maltitol and isomaltitol, hydrogenated starch hydrolysates and hydrogenated glucose syrups found in corn syrups for example, and artificial sweeteners such as free saccharin acids, water soluble salts of saccharin, cyclamate salts, palatinin, dihydrochalcones, glycyrrhizin, L-aspartyl-L-phenylalanine methyl ester, amino acid based sweeteners, talin, steviosides, dihydrochalcone compounds, acesulfame salts and mixtures thereof. A mixture of sucrose in water (liquid sugar) and corn syrup is particularly preferred.

The preparations may also include colorants, buffers, acidulants, flavorants and other conventional additives.

The flavoring agents may comprise oils derived from plants, leaves, flowers, fruit etc. Representative flavor oils of this type include citrus oils such as lemon oil, orange oil, lime oil, grapefruit oil, fruit essences such as apple essence, pear essence, peach essence, strawberry essence, apricot esence, raspberry essence, cherry essence, plum essence, pineapple essence, as well as the following essential oils: peppermint oil, spearmint oil, mixtures of pepermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors such as mixed fruit, may also be incorporated.

The colorants useful in the present invention include the pigments and dyes suitable for food, drug and cosmetic applications. The acceptable materials are preferably water-soluble.

The lozenges of the invention can be prepared batchwise by heating the sweetener at temperatures between about 250° F. and 325° F., and removing residual moisture by evacuation. Flavorants and colorants, if desired, are then added to the sugar mass. The silver compound is then added in powdered form and mechanically kneaded into the viscous mass until uniformly distributed. The mass is allowed to cool and is reduced in size in a batch former, then a rope sizer, and finally to a lozenge die former. In the case of a continuous process the silver compound is added to a stream of heated sweetener mass in a warm buffered acetic acid or phospheric acid solution.

In the case of a chewing gum as the oral preparation, a gum base is prepared by heating and blending various ingredients, such as natural gums, synthetic resin, waxes, plasticizers, etc. in a manner well known in the art. Typical examples of the ingredients found in a chewing gum base are masticatory substances of synthetic origin such as styrene-butadiene copolymer, isobutylene-isoprene copolymer, polyisobutylene, polyethylene, petroleum wax, polyvinyl acetate, as well as masticatory substances of natural origin such as rubber latex solids, chicle, crown gum, mispero, rosidinha, jelutong, pendare, perillo, niger gutta, tunu, etc. The elastomer is normally employed in an amount within the range of about 5% to about 35%, preferably from about 15% to 30%, and optimally from about 18% to about 25% by weight of the total chewing gum composition.

The chewing gum composition may also include solvents, detackifiers, waxes, softening agents, acidulants, buffers, lubricants, fillers, emulsifiers, colorants, antioxidants and/or texturizers, bulking agents and other conventional ingredients as will be apparent to those skilled in the art.

The gums may also contain binders which include gum arabic, xanthan gum, gum tragacanth, topiocadextrin, or modified food starch with gum arabic being preferred.

The gums are prepared by melting the gum base at elevated temperatures and adding thereto the sweetener and silver compound as well as additional flavorants, colorants, binders or other additives. The mixture is mixed until homogeneous, cooled, rolled into sheets and scored to form the shaped gum.

In the case of anti-smoking oral preparations comprising a mouthwash, spray or rinse, the vehicle is typically a water-alcohol mixture. Generally the ratio of total water to alcohol is in the range of from about 1:1 to about 20:1, preferably about 3:1 to about 20:1 and most preferably about 3:1 to about 10:1 by weight. The total amount of water-alcohol mixture in a mouthwash preparation is typically in the range from about 45% to about 82.5% by weight of the composition. The pH value of such mouthwash preparations is generally from about 4 to about 9 and preferably from about 5 to about 7. A pH below 4 is irritating to the oral cavity and a pH greater than 9 results in an unpleasant mouth feel.

Fluorine providing compounds may also be present in the oral preparations of this invention. These compounds may be slightly water soluble or may be fully water soluble and are characterized by their ability to release fluoride ions or fluoride-containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid preparation such as a mouthwash, the fluorine providing compound is generally present in an amount sufficient to release up to about 0.15%, preferably about 0.001% to about 0.1% and most preferably from about 0.001% to about 0.05% fluoride by weight of the preparation. The silver compound and sweetener may be added to the vehicle with mixing along with the additional additives.

The oral preparation may also contain additional flavorants and colorants, acidulants and buffers.

The anti-smoking oral preparations may also be substantially solid or pasty in character such as a dental cream, toothpaste or a toothpowder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. For toothpaste and dental creams the water content is about 25% to 50% by weight.

In clear gels, a polishing agent of colloidal silica and alkali metal aluminosilicate complexes are preferred since they have refractive indicies close to the refractive indicies of gelling agent liquid systems commonly used in dentifrices.

The silver compound and sweetener is added at any convenient point along with acidulants and/or buffers.

In order to more completely describe the present invention the following Examples are given.

EXAMPLE 1

This Example demonstrates a batch preparation of a silver acetate containing lozenge according to the invention.

A liquid sugar containing 67% sucrose by weight and corn syrup having a dextrose equivalent of 42 (42 D.E.) and containing 80% carbohydrate by weight and 20% water by weight were combined and heated in a closed agitated cooker to between 285° F. and 305° F. The resulting viscous liquid was passed through a vacuum chamber to reduce residual moisture to between 1% and 5%. An artificial cherry flavor (Fritzchie, Dodge & Olcott) and a red colorant (COLORCON Red 3 & 40) as a mixture (Colorcon Corp.) was then added to the hot viscous liquid in a receiving kettle. The viscous mass was then moved to a kneading table where powdered silver acetate was added thereto and mechanically kneaded for about 4 to 8 minutes until uniformly dispersed. The mass was allowed to cool and then reduced in size in a batch former, then a rope sizer and finally to a lozenge die former. The so-formed lozenges were air cooled on a conveyor and then bunch wrapped.

Table 1 below summarizes the weight composition of the lozenge.

TABLE 1

| Ingredients | Weight |
| --- | --- |
| Liquid Sugar | 82 lbs. |
| 67% Sucrose | 55 lbs. |
| 33% Water | 27 lbs. |
| Corn Syrup (42 D.E.) | 56 lbs. |
| 80% Carbohydrate | 45 lbs. |
| 20% Water | 11 lbs. |
| Artificial Cherry Flavor | 0.25 lbs. (113 grams) |
| Color | 3 tablespoons |
| Silver Acetate | 0.117 lbs. (53 grams) |

The total solid content after processing was 100 lbs.

EXAMPLES 2 & 3

These Examples demonstrate a comparison of the taste and smoking deterrence between a lozenge containing a high level of silver acetate (Ex. 2-6 mg.) and a lozenge containing a significantly lower level of silver acetate (Ex. 3-2.5 mg.). All lozenges were prepared according to the procedure of Example 1. In each Example, smokers were asked to dissolve a lozenge in their mouths for about 30 seconds, then light a cigarette and comment on the taste. There were about 52 smokers as a sample for Example 2 and 120 smokers as a sample in Example 3. A result was considered acceptable if the smoker did not comment about any odd or bitter taste before or after smoking and a result was considered not-acceptable if the smoker volunteered that the taste was offensive or words to that effect or expelled the lozenge.

Tables 2 and 3 summarize the results of each of Examples 2 and 3.

TABLE 2

|  | % Taste Before Smoking | % Taste After Smoking |
| --- | --- | --- |
| Acceptable | 47 | 5 |
| Not-acceptable | 53 | 95 |

TABLE 3

|  | % Taste Before Smoking | % Taste After Smoking |
| --- | --- | --- |
| Acceptable | 88 | 7 |
| Not-acceptable | 12 | 93 |

The 6 mg. silver acetate lozenge of Example 2 (2 mg. silver acetate/gram sucrose base) showed borderline taste acceptability, but good effectiveness as a smoking deterrent lozenge. The 2.5 mg. silver acetate lozenge of Example 3 (1 mg. silver acetate/gram sucrose base) showed both good taste acceptability and good effectiveness as a smoking deterrent lozenge. It was also observed that some smokers cannot detect the metallic-bitter taste response of either the silver acetate lozenge with or without smoke. It was assumed that these individuals either lacked the genetic ability to taste silver and its reaction products with smoke at the concentrations tested, or have damaged taste sites.

The results indicate that a small amount of free uncomplexed silver ions when combined with a sweetener had good taste acceptability and demonstrate effective smoking deterrence.

In addition, it was observed that even in the case of Example 3, most of the smokers put their cigarette out and expelled the lozenge before approximately 10% of the lozenge was dissolved indicating that only 0.25 mg. of silver acetate is required to effect a smoking deterrent response.

Thus the invention provides anti-smoking oral preparations containing dilute silver acetate concentrations and a sweetener which offers the following advantages.

1. Eliminates the requirement for complexing with ammonium salts or amines.
2. Reduces the cost of the preparation due to reduced silver compound levels.
3. Provides greater flexibility in formulating various oral preparations and improves taste.
4. Lowers the consumption and absorption of the silver compound in the body; and
5. Delivers a uniform and targeted concentration of silver ion to the mouth to improve the efficiency of the silver compound as a smoking deterrent.

I claim:

1. A lozenge having an acceptable taste upon dissolution in the absence of smoking but providing an unpleasant taste upon smoking, the sole smoking deterrent active ingredient in said lozenge consisting essentially of from 0.1 mg to not more than 2.5 mg of silver acetate uniformly distributed in a lozenge base, said lozenge providing a uniform release of said silver acetate upon dissolution of said lozenge base in the mouth, said lozenge base containing as its major component a quantity of sweetener sufficient to produce a ratio of sweetness intensity to silver acetate of from 100:1 to 2500:1.

2. A lozenge according to claim 1 wherein the amount of silver acetate uniformly distributed in the lozenge base is from 0.5 to 2 mg.

3. A lozenge according to claim 1 wherein the ratio of sweetness intensity to silver acetate is from 500:1 to 1000:1.

4. A lozenge according to claim 1 wherein the sweetener comprises sucrose.

5. A lozenge according to claim 1 wherein the sweetener comprises corn syrup.

6. A lozenge according to claim 1 wherein the sweetener is a mixture of sucrose and corn syrup.

* * * * *